(12) United States Patent
Al Ahmad

(10) Patent No.: US 10,078,067 B2
(45) Date of Patent: Sep. 18, 2018

(54) APPARATUS AND METHOD FOR DETECTION AND QUANTIFICATION OF BIOLOGICAL AND CHEMICAL ANALYTES

(71) Applicant: United Arab Emirates University, Al Ain (AE)

(72) Inventor: Mahmoud Al Ahmad, Al Ain (AE)

(73) Assignee: United Arab Emirates University, Al Ain (AE)

( * ) Notice: Subject to any disclaimer, the term of this patent is extended or adjusted under 35 U.S.C. 154(b) by 0 days.

(21) Appl. No.: 15/121,958

(22) PCT Filed: Aug. 25, 2014

(86) PCT No.: PCT/IB2014/064042
§ 371 (c)(1),
(2) Date: Aug. 26, 2016

(87) PCT Pub. No.: WO2016/030713
PCT Pub. Date: Mar. 3, 2016

(65) Prior Publication Data
US 2017/0160232 A1 Jun. 8, 2017

(51) Int. Cl.
*G01N 27/48* (2006.01)
*G01N 27/447* (2006.01)

(52) U.S. Cl.
CPC ....... *G01N 27/48* (2013.01); *G01N 27/44752* (2013.01)

(58) Field of Classification Search
CPC .......................... G01N 27/48; G01N 27/44752
USPC ........................................................ 324/71.1
See application file for complete search history.

(56) References Cited

U.S. PATENT DOCUMENTS

| 4,058,446 | A | 11/1977 | Zirino et al. |
| 6,541,617 | B1 * | 4/2003 | Bamdad .................. B01J 13/00 |
| | | | 435/287.2 |
| 2004/0124084 | A1 | 7/2004 | Lee et al. |
| 2017/0095611 | A1 * | 4/2017 | Wang .................. A61M 5/1723 |

(Continued)

FOREIGN PATENT DOCUMENTS

| EP | 1688742 A1 | 9/2006 |
| WO | 2010006253 A1 | 1/2010 |

(Continued)

OTHER PUBLICATIONS

International Search Report, International Patent Application No. PCT/IB2014/064042, dated Jan. 14, 2015, 6 pages.

(Continued)

*Primary Examiner* — Christopher Mahoney
(74) *Attorney, Agent, or Firm* — Fitch, Even, Tabin & Flannery LLP

(57) ABSTRACT

A sensing device and a sensing method for operating the same are disclosed. An analytical sample is subjected to an electric field within a sample chamber using at least two electrodes. Initially, a holding voltage is provided such that the analyte in the analytical sample polarizes and diffuses towards one of the electrodes forming an electrode-electrolyte interface. Subsequently, a pulsating sweep voltage is provided across the two electrodes. A current-voltage profile and/or a capacitance-voltage profile of the analytical sample are determined. The analyte is identified and quantified based on the current-voltage profile and capacitance-voltage profile respectively.

12 Claims, 5 Drawing Sheets

(56) References Cited

U.S. PATENT DOCUMENTS

2017/0173578 A1* 6/2017 Crooks .................. B01L 3/5027
2017/0350848 A1* 12/2017 Wang .................. G01N 33/0057

FOREIGN PATENT DOCUMENTS

WO        2010099618 A1    9/2010
WO        2010126897 A1    11/2010

OTHER PUBLICATIONS

Written Opinion of the International Searching Authority, International Patent Application No. PCT/IB2014/064042, dated Jan. 14, 2015, 7 pages.
Extended European Search Report in corresponding European Application No. 14900596.9, dated Feb. 28, 2018, 9 pages.

* cited by examiner

APPARATUS AND METHOD FOR DETECTION AND QUANTIFICATION OF BIOLOGICAL AND CHEMICAL ANALYTES

BACKGROUND OF THE PRESENT INVENTION

Technical Field

The present invention generally relates to detection and quantification of an analyte of interest. More specifically, the present invention relates to an apparatus and a method for detecting and quantifying biological and chemical analytes.

Description of the Related Art

Detection and quantification of various biological and chemical analytes has applications in a myriad of fields of use across many industries, including but not limited to, medical diagnostics, genomics and proteomics, food and beverage industry, national security and defence, and environmental monitoring.

Accordingly, reliable, time-efficient, and cost-effective identification and/or quantification of biological and chemical analytes are important fields of research across many industries.

In recent years, several sensing modalities for detection and/or quantification of biological and chemical analytes have been proposed.

One of the conventional techniques is based on fluorescence exhibited by many analytes of interest. According to this technique, visible markers are attached to analytes and also, a complex optical assembly including high intensity optical sources, optical filters and lenses, is then used to detect frequency range of emission, which serve to characterise an analyte of interest. Although such techniques provide good selectivity and sensitivity, the fluorescence-based sensing devices are inherently cumbersome, time-consuming, expensive, and accordingly, not suited for many applications such as point-of-care diagnostics.

In recent years, several methods based on antigen or genome detection have been proposed. One example of such methods is Enzyme Linked Immuno Sorbent Assay (ELISA) based protocols. However, such methods are virus specific and suffer from a limited dynamic range of detection. Other quantitative real-time methods such as polymerase chain reaction, flow cytometry, and techniques revealing viable cell size, have also been developed to aid determination of virus and other micro-organisms.

Another solution is the use of transmission electron microscopy (TEM) and different mass spectroscopy techniques. While these techniques are able to provide accurate and reliable information related to size and charge; they cannot characterize particles in their liquid environment and are expensive and time consuming. Moreover, these techniques require relatively high concentrations of the target analyte, which is impossible during the early diagnosis of many diseases.

A wide range of organic and inorganic materials typically found in biological and chemical analytes are known to be exhibit electrical properties. In the prior art, various techniques harnessing the electrical properties of such materials, in particular, the polarization response such materials to an external electric field have also been proposed.

Typical electrical-based detection and/or quantification modalities are designed to sense changes in electrical properties of an electrode surface functionalised using probes designed to bind to specific analytes of interest. Different types of electrochemical sensors such as charge transfer sensors, capacitance-based sensors, impedance-based sensors, and field-effect based sensors have been reported.

However, the currently available electrochemical sensors suffer from several disadvantages. The devices are expensive and restricted to detection of usually a single analyte. Several such devices are not conducive to reuse. These techniques invariably require extensive sample preparation such as sample staining using labels, biomarkers and so on. Moreover, the response time is undesirably high. In addition, such devices are usually bulky and not suitable for point-of-care applications.

In light of the foregoing, there is a need for reliable, time-efficient, and cost-effective identification and/or quantification of biological and chemical analytes.

SUMMARY OF THE PRESENT INVENTION

It is an object of the present invention to provide a sensing method for label free, reliable, rapid, and low-cost identification and quantification of biological and chemical analytes.

It is an object of the present invention to provide a sensing device for label free, reliable, rapid, and low-cost identification and quantification of biological and chemical analytes.

The objects are achieved by providing embodiments of the present invention relating to a sensing method and a sensing device based on said method. Further embodiments of the present invention are also provided.

The underlying concept of the present invention is to exploit electrical properties, in particular, tendency to be polarised in presence of electrical fields, of various biological and chemical analytes of interest to develop a technique wherein such analytes are modelled in a manner analogous to that used for measurement of dopant profile in semiconductor materials. Accordingly, an analytical sample is subjected to a varying electrical field established across two electrodes disposed within a sample chamber and current-voltage and capacitance-voltage profiles are measured. Based on these profiles, various equivalent electrical parameters such as leakage current, conductivity, ideality parameter, electrical mobility, and doping concentration are derived in a manner akin to theory of semiconductors. To take into account electrical properties of medium carrying the analyte, reference parameters are evaluated for such medium that is known to be devoid of the analyte of interest. The identification and quantification is carried out based on various sampled values after factoring in the reference values.

In a first aspect of the present invention, a sensing method for detecting an analyte in an analytical sample is provided. At a first step, the analytical sample is supplied to a sample chamber. The sample chamber is at least partially delimited by a first electrode and a second electrode. Initially, a holding voltage is provided across the first and second electrodes such that a potential gradient is formed across the sample chamber, whereby the analyte polarizes and diffuses towards one of the electrodes forming an electrode-electrolyte interface. Subsequently, a pulsating sweep voltage is provided across the first and the second electrodes and a current-voltage profile of the analytical sample is determined. Finally, the analyte is identified based on the current-voltage profile.

In a second aspect of the present invention, a sensing method for quantifying an analyte in an analytical sample is provided. At a first step, the analytical sample is supplied to a sample chamber. The sample chamber is at least partially delimited by a first electrode and a second electrode. Initially, a holding voltage is provided across the first and second electrodes such that a potential gradient is formed across the sample chamber, whereby the analyte polarizes and diffuses towards one of the electrodes forming an electrode-electrolyte interface. Subsequently, a pulsating sweep voltage is provided across the first and the second electrodes and a capacitance-voltage profile of the analytical sample is determined. Finally, the analyte is quantified based on the capacitance-voltage profile.

In a third aspect of the present invention, a sensing device for detecting an analyte in an analytical sample is provided. The sensing device comprises a sample chamber, a first electrode and a second electrode, a controlled voltage source, and a measurement module. The sample chamber is configured for holding the analytical sample. The first electrode and the second electrode at least partially delimit the sample chamber. The controlled voltage source is electrically coupled to the first and the second electrodes, and is configured for providing a holding voltage and a pulsating sweeping voltage across the first and the second electrodes, during different stages of operation of the sensing device such that a potential gradient is formed across the sample chamber. The measurement module is configured for measuring variation of an electrical current through the sample chamber under a varying voltage applied across the electrodes to generate a current-voltage profile of the analytical sample. The measurement module is further configured for identifying the analyte in the analytical sample based on the current-voltage profile.

In a fourth aspect of the present invention, a sensing device for quantifying an analyte in an analytical sample is provided. The sensing device comprises a sample chamber, a first electrode and a second electrode, a controlled voltage source, and a measurement module. The sample chamber is configured for holding the analytical sample. The first electrode and the second electrode at least partially delimit the sample chamber. The controlled voltage source is electrically coupled to the first and the second electrodes, and is configured for providing a holding voltage and a pulsating sweeping voltage across the first and the second electrodes, during different stages of operation of the sensing device such that a potential gradient is formed across the sample chamber. The measurement module is configured for measuring variation of a capacitance across the first and the second electrodes under a varying voltage applied across the electrodes to generate a capacitance-voltage profile of the analytical sample. The measurement module is further configured for quantifying the analyte in the analytical sample based on the capacitance-voltage profile.

Accordingly, the present invention provides a sensing device and a sensing method for identification and quantification of biological and chemical analytes. The techniques of the present invention facilitate label free, reliable, rapid, and low-cost identification and quantification.

The techniques of the present invention advantageously do not require elaborate sample preparation such as labelling using biomarkers, staining, and so on. Thus, the techniques of the present invention facilitate label free identification and quantification.

The sensing device and the sensing method of the present invention are advantageously not limited to any specific analytes. The techniques of the present invention are only reliant on tendency of an analyte to polarise when subjected to an electric field and hence, are applicable to identification and quantization of a wide range of analytes of interest.

The sensing device of the present invention is advantageously reusable for practically unlimited number of identification and quantification operations. Prior to each operation, the sample chamber in the sensing device may be flushed using a buffer solution such as Phosphate-buffered saline (PBS) to ensure no residues from a previous operation impact the measurement in the next operation.

BRIEF DESCRIPTION OF THE DRAWINGS

The present invention is further described hereinafter with reference to illustrated embodiments shown in the accompanying drawings, in which.

DETAILED DESCRIPTION OF THE PRESENT INVENTION

Figure 1:
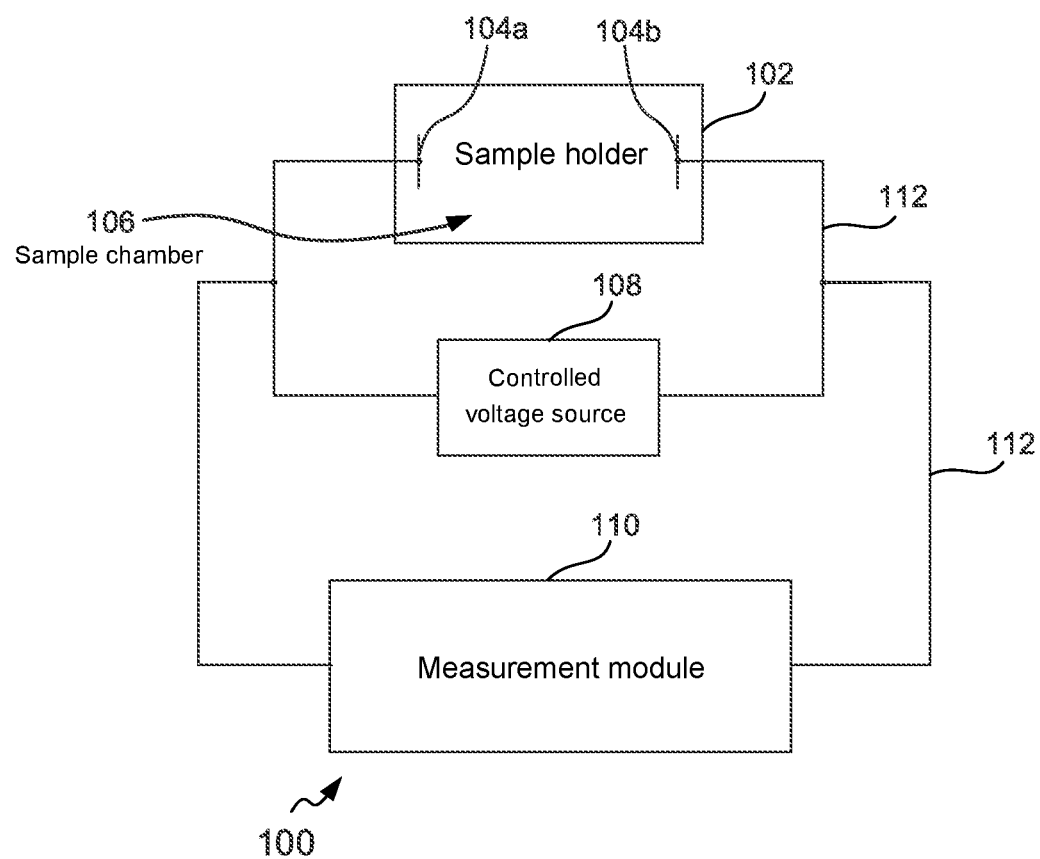
FIG. 1 illustrates a schematic view of a sensing device for identification and quantification of an analyte in an analytical sample in accordance with various exemplary embodiments of the present invention.

Various embodiments are described with reference to the drawings, wherein like reference numerals are used to refer to like elements throughout. In the following description, for purpose of explanation, numerous specific details are set forth in order to provide a thorough understanding of one or more embodiments. It may be evident that such embodiments may be practised without these specific details.

The techniques of the present invention are applicable for identification and quantification of any biological and chemical analytes of interest. The techniques of the present invention are not restricted to any specific field of use. The only caveat for use of the techniques of the present invention is that the analyte of interest should be able to exhibit polarisation when subjected to an electric field.

While in the description provided hereinafter, the sample of interest may be indicated to be fluidic, the techniques of the present invention are in no manner limited to fluidic samples and are equally applicable to solid samples.

Various exemplary analytes include, but not limited to, various biological entities such as micro-organism or parts thereof, that is, bacteria, micro-algae, fungi, virus, and so on, and DNA, RNA, or any other inter-cellular bodies thereof. In addition, several chemical species, both organic and inorganic, in ordinary form or in the form of nano-particles, can be successfully identified and quantified using the techniques of the present invention.

By way of example, the techniques of the present invention can be successfully applied to detect and quantify virus present in a sample of bodily fluid or tissue sample.

The strength of polarisation exhibited by a virus cell depends on the compositions of the virus and its interaction with the medium polarity. Usually all viruses are coated with proteins and contain genetic material, which can be either RNA or DNA. Since both RNA and DNA have phosphordiester bonds, the genetic material carries a partial negative charge. On the other hand, various proteins are also present within a virus cell. These proteins could be neutral, negative, or positive in charge. The net charge of a virus cell depends on the cumulative charges of the genetic material and the proteins therein.

The electric field distribution through an analytical sample containing virus cells is altered in magnitude and phase in a manner dependent on biological configuration and its relative concentration in the analytical sample. The virus particle essentially acts as an electrical dipole, and presents electrical discontinuities in a manner akin to those presented by dopant impurities added to semiconductor materials.

Advantageously, the techniques of the present invention are able to identify and quantify whole cells and hence, do not require expensive procedures to extract genetic material from within the target cells.

As noted previously, the present invention is generally being explained herein in the context of fluidic samples. However, this is only intended to explain the techniques of the present invention in an easily understandable manner and not to limit the present invention in any manner. The techniques of the present invention are equally applicable to solid samples.

Having said that, it will be appreciated that any non-fluidic samples derived from an animal or a plant subject could be converted into a colloidal suspension for analysis to form a 'liquid' analytical sample.

Referring now to FIG. 1, a schematic view of a sensing device 100 for identification and quantification of an analyte in an analytical sample is depicted in accordance with various exemplary embodiments of the present invention.

The sensing device 100 includes a sample holder 102, a controlled voltage source 108, and a measurement module 110.

The sample holder 102, the controlled voltage source 108, and the measurement module 110 are operatively coupled using interconnections 112. The sample holder 102 includes a first electrode 104*a* and a second electrode 104*b* (collectively referred to as electrodes 104 and individually, as electrode 104) and a sample chamber 106.

The sample chamber 106 is configured for holding the analytical sample. The first electrode 104*a* and the second electrode 104*b* at least partially delimit the sample chamber 106 in such manner that when the analytical sample is supplied to the sample chamber 106, the analytical sample is in fluidic contact with each of the electrodes 104.

Referring to FIG. 2A, a perspective view of a sample holder 102 is depicted in accordance with an exemplary embodiment of the present invention.

In this exemplary embodiment, a cylindrical container with conductive lateral wall and insulating base is provided. A cylindrical rod with diameter in the range of about $\frac{1}{10}^{th}$ of that of the cylindrical container and made of an electrically conductive material is disposed within the cylindrical container such that the cylindrical rod acts as the first electrode 104*a* and the lateral wall of the cylindrical container acts as the second electrode 104*b*. The internal cavity of the cylindrical container sans the volume of the cylindrical rod serves as the sample chamber 106.

A cross-sectional view of the sample holder 102 along A-A' is depicted in FIGS. 2B and 2C before and after application of a holding voltage, as will be explained below.

Referring back to FIG. 1, the controlled voltage source 108 is electrically coupled to the electrodes 104 through interconnections 112, as can be seen from the adjoining figure. The controlled voltage source 108 is configured for providing a holding voltage and a pulsating sweeping voltage across the electrodes 104, such that a potential gradient is formed across the sample chamber.

During each identification and quantification operation, the controlled voltage source 108 provides a holding voltage for an initial period of time, which may be referred to as 'holding time'. The holding voltage is typically a low voltage in the order of few millivolts and the holding time is typically in the range of a few seconds to a few minutes. The holding voltage applied across the electrodes 104 for duration of the holding time ensures that the analyte in the analytical sample polarises and slowly diffuses towards one of the electrodes 104 to form an electrode-electrolyte interface and thereby, reaches a state of equilibrium.

Referring now to FIGS. 2B and 2C, cross-sectional views depicting distribution of analyte within the analytical sample before and after application of a holding voltage are depicted.

As evident from these figures, the analyte of interest is evenly distributed in the analytical sample prior to application of the holding voltage. As the holding voltage is applied, the analyte slowly diffuses towards one of the electrodes 104 to form an electrode-electrolyte interface therewith and eventually, the analytical sample reaches a state of equilibrium after being subjected to the holding voltage for the holding time. The holding time may be adjusted according to the analytical sample under evaluation to ensure that the desired state of equilibrium is reached before application of pulsating sweep voltage.

Referring back to FIG. 1, subsequent to application of the holding voltage for a suitable duration of holding time, the measurement module 110 provides a pulsating sweep voltage across the electrodes 104. The pulsating sweep voltage is achieved through superimposing a small AC voltage on a sweeping DC voltage. It should be noted that the DC voltage is ramped up in steps while providing sufficient time at each step to achieve a state of equilibrium.

The measurement module 110 measures variation of an electrical current through the sample chamber 106 and/or capacitance across the electrodes 104 under the pulsating sweep voltage applied across the electrodes to generate a current-voltage profile and/or capacitance-voltage profile of the analytical sample. The measurement module 110 identifies the analyte using the current-voltage profile. The measurement module 110 quantifies the analyte using the capacitance-voltage profile.

It should be noted that various electrical properties of the analytical sample as measured using the measurement module 110 represent the cumulative effect of the electrical properties of the analyte and a medium carrying the analyte, that is, the matrix of the analytical sample.

As will be appreciated, to determine the electrical properties attributable to the analyte present in the analytical sample, it is imperative to take into account the electrical properties of the medium or the matrix present in the analytical sample.

To this end, a reference sample that is known to be devoid of the analyte is selected, and equivalent electrical properties of such reference sample are determined using the same techniques as those used for determining electrical properties of an analytical sample, and as will be explained a little later in the following description.

Various examples of such electrical properties include, but are not limited to, Debye volume, electrical mobility, and dopant concentration, which are, hereinafter referred to as reference Debye volume, reference electrical mobility, and reference dopant concentration respectively.

In practice, it is contemplated that a database of electrical properties of a set of reference samples is prepared and an appropriate reference sample and the corresponding set of electrical properties are selected for a given analytical sample.

In the field of medical diagnostics, such reference sample could be, for example, whole blood, plasma, serum, colloidal solutions formed from other bodily samples, and so on, taken from healthy individuals. Similar reference samples could be selected for other fields of use of the present invention.

These aspects of the present invention will be further elaborated in the following description.

In various exemplary embodiments of the present invention, the measurement module 110 calculates the Debye volume of the analytical sample ($\phi_S$) as well as a corresponding reference sample ($\phi_R$). The Debye volume ($\lambda$) is calculated from the Debye length in electrolytes or a colloidal suspension as given by the following equation:

$$\lambda = \sqrt{\frac{\varepsilon_r \varepsilon_0 k_B T}{2 N_A e^2 I}} \tag{1}$$

In a first embodiment of the present invention, the measurement module 110 identifies the analyte in the analytical sample based on the current-voltage profile, as will now be explained.

It was empirically identified that when subjected to the measurement techniques of the present invention, each analyte exhibits a unique material index 77 that can be used to uniquely identify the analyte in an analytical sample.

The measurement module 110 determines the material index 77 as explained below.

The measurement module 110 measures variation of the electrical current through the sample chamber 106 under the pulsating sweep voltage applied across the electrodes to generate a current-voltage profile of the analytical sample.

Figure 3:
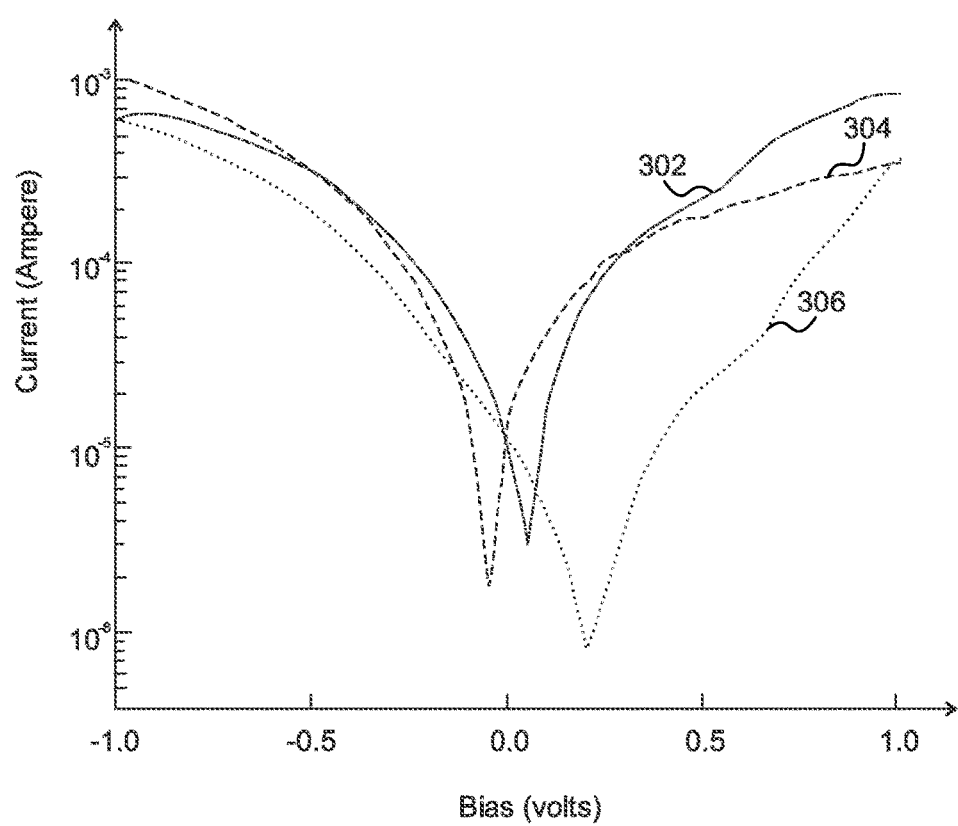
FIG. 3 illustrates an exemplary current-voltage profile of an analytical sample in accordance with various exemplary embodiments of the present invention.

An exemplary current-voltage profile is depicted in FIG. 3. As can be seen from the adjoining figure, profile 302 corresponds to the reference sample, while profiles 304 and 306 correspond respectively to two different analytical samples.

The measurement module 110 determines leakage current and conductivity of the analytical sample. These parameters are referred to as 'sample leakage current' and 'sample conductivity' respectively.

The measured current is known to be related to leakage current, conductivity, and voltage according to the following equation:

$$I = I_0 + \sigma V + k V^2 + \gamma V^3 \tag{2}$$

where,
I is measured current,
V is applied voltage,
$I_0$ is sample leakage current,
$\sigma$ is sample conductivity, and
k, $\gamma$ are voltage coefficients.

Using the current-voltage profile of the analytical sample, the measurement module 110 determines the sample leakage current and the sample conductivity.

The measurement module 110 then evaluates the ideality parameter of the analytical sample. The ideality parameter is derived using the following equation:

$$I = I_s e^{\frac{qV}{nKT}} \tag{3}$$

where,
I is measured current,
V is applied voltage,
$I_S$ is sample leakage current,
q is electron charge,
n is ideality parameter,
K is Boltzmann Constant, and
T is absolute temperature.

Finally, the measurement module 110 calculates the sample electrical mobility based on the sample conductivity and the sample ideality parameter, as per the following equation:

$$\mu = \frac{\sigma}{nq} \tag{4}$$

where,
$\mu$ is electrical mobility
q is electron charge, and
n is ideality parameter.

The electrical mobility of a suitable reference sample is determined using the same sequence of steps, as described above for calculation of electrical mobility of the analytical sample.

The measurement module 110 determines the material index as modulus of a ratio of deviation of the sample Debye volume from a reference Debye volume and deviation of the sample electrical mobility from a reference electrical mobility, wherein the material index uniquely corresponds to the analyte, whereby the analyte is identified.

As sample electrical mobility $\mu_S$ and reference electrical mobility $\mu_R$ are known, the material index $\eta$ of the analyte of interest is calculated using the following equation:

$$\eta = \frac{|\phi_S - \phi_R|}{|\mu_S - \mu_R|} \tag{5}$$

According to the techniques of the present invention, it is contemplated that a data set of material indices of various known analytes of interest is developed and is cross-referenced for identification of an unknown analyte in a given analytical sample.

In an alternative embodiment, the material index $\eta$ may be calculated as a range of values for a given analyte. In this case, the material index $\eta'$ is calculated as follows:

$$\eta' = \left| \left(\frac{\phi_S}{\mu_S}\right) - \left(\frac{\phi_R}{\mu_R}\right) \right| \tag{6}$$

The range of material index is calculated as follows:

$$\nabla \eta = \eta \pm |\eta - \eta'| \tag{7}$$

In a second embodiment of the present invention, the measurement module 110 quantifies the analyte in the analytical sample based on the capacitance-voltage profile, as will now be explained.

The measurement module 110 measures variation of the electrical capacitance across the electrodes 104 under the pulsating sweep voltage applied across the electrodes to generate a capacitance-voltage profile of the analytical sample.

Figure 4:
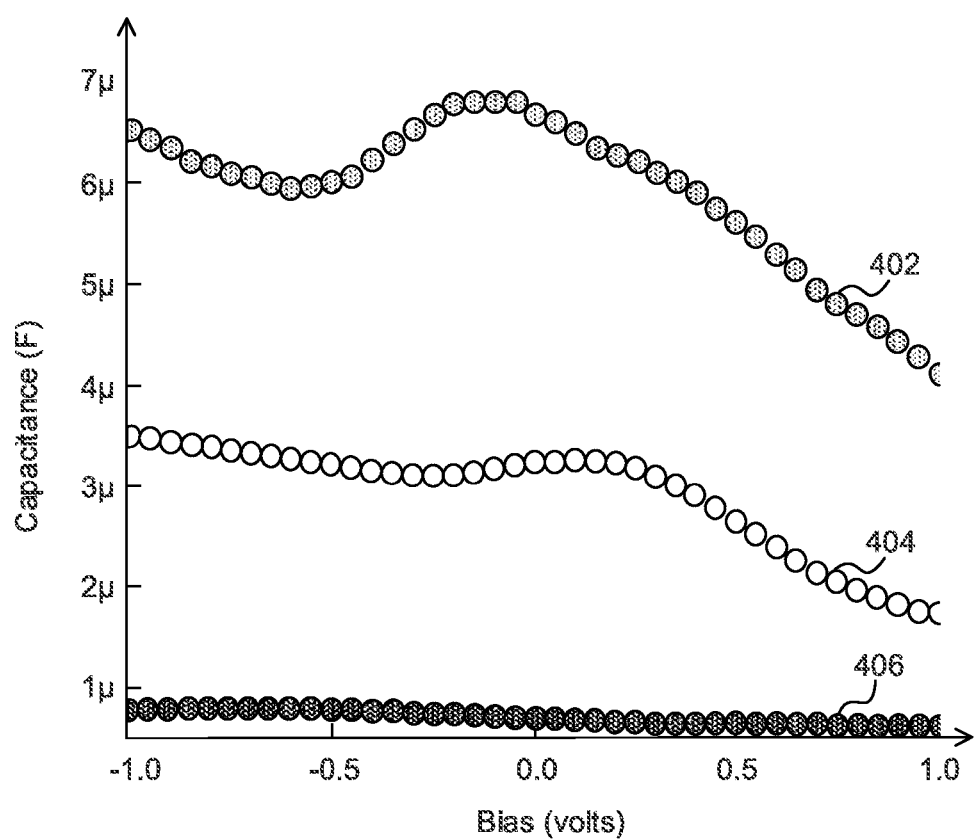
FIG. 4 illustrates an exemplary capacitance-voltage profile of an analytical sample in accordance with various exemplary embodiments of the present invention.

An exemplary capacitance-voltage profile is depicted in FIG. 4. As can be seen from the adjoining figure, profile 402 corresponds to the reference sample, while profiles 404 and 406 correspond respectively to two different analytical samples.

In accordance with the theory of semiconductors, the doping concentration in a substrate may be determined using a capacitance-voltage profile generated using Schottky diode arrangement or more recently, using a metal-oxide semiconductor capacitor arrangement. The doping concentration is known to be inversely proportional to the slope of plot of capacitance ($1/C^2$) and voltage (V).

The doping concentration in terms of capacitance and voltage is given by the equation:

$$N = \left| \left( 0.5 q \varepsilon A^2 \frac{d(1/C^2)}{dV} \right)^{-1} \right| \quad (8)$$

where,
N is dopant concentration,
q is electron charge,
ε is permittivity,
A is area of electrode,
C is measured capacitance, and
V is applied voltage.

Figure 2A:
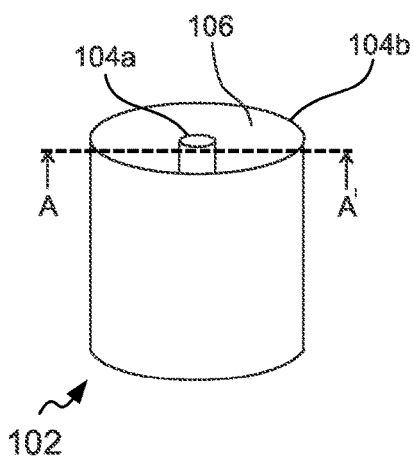
FIGS. 2A-2C illustrate respectively a perspective view, a cross-sectional view prior to application of holding voltage, and a cross-sectional view subsequent to application of holding voltage of a sample holder in accordance with an exemplary embodiment of the present invention.
Figure 2B:
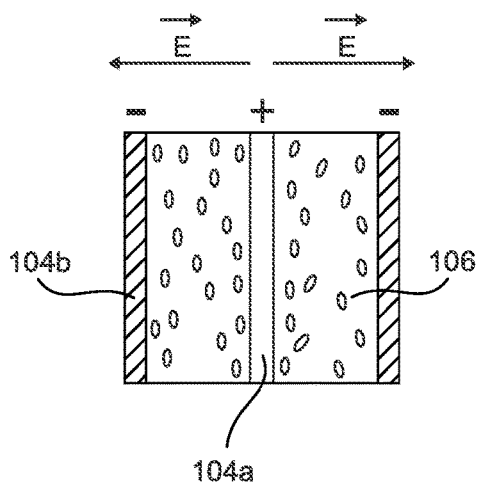
Figure 2C:
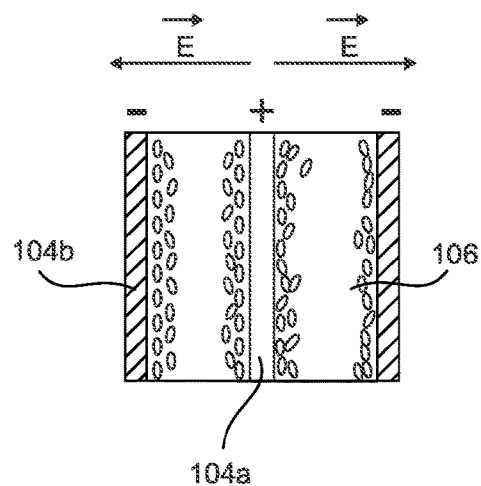

It should be noted that in case of asymmetrical electrodes with unequal surface areas such as in case of the exemplary assembly shown in FIG. 2, dopant concentration is calculated theoretically through consideration of infinitesimally thin slices of the analytical sample between the two electrodes, which theoretically provides the same electrode surface areas. The incremental dopant density is then mathematically integrated over the entire volume of the sample chamber 106 to derive the value of dopant concentration N.

The measurement module 110 determines a sample doping concentration ($N_S$) and a reference doping concentration ($N_R$).

The measurement module 110 determines quantity of an analyte (in terms of number of units) in a given sample as modulus of a ratio of deviation of the sample doping concentration from a reference doping concentration and deviation of the sample Debye volume from a reference Debye volume. Mathematically, the quantity of analyte is expressed using the following equation:

$$\Lambda = \frac{|N_S - N_R|}{|\phi_S - \phi_R|} \quad (9)$$

where,
Λ is total quantity of the analyte in the analytical sample

In an alternative embodiment, the quantity of the analyte Λ may be calculated as a range of values for a given analyte. In this case, the quantity of the analyte Λ' is calculated as follows:

$$\Lambda' = \left| \left( \frac{N_S}{\phi_S} \right) - \left( \frac{N_R}{\phi_R} \right) \right| \quad (10)$$

The range of material index is calculated as follows:

$$\nabla \Lambda = \Lambda \pm |\Lambda - \Lambda'| \quad (11)$$

In an alternative embodiment, if the unit volume of the analyte identified in accordance with the first embodiment of the present invention, the measurement module 110 determines the analyte quantity as modulus of a ratio of deviation of the sample Debye volume from a reference Debye volume and a unit volume of the analyte. Thus, mathematically, the quantity of analyte is expressed using the following equation:

$$\Lambda = \frac{|\phi_S - \phi_R|}{\upsilon} \quad (12)$$

where,
Λ is total quantity of the analyte in the analytical sample
v is unit volume of the analyte In an exemplary embodiment of the present invention, the measurement module may be implemented using a simple microprocessor embedded within the sensing device. The microprocessor is provided with the requisite programming code to compute various electrical parameters, as explained above. In an exemplary embodiment of the present invention, the measurement module 110 is also provided with control instructions for timing the generation of the holding voltage and the pulsating sweep voltage during operation of the sensing device 100. The sensing device may additionally be provided with a persistent memory storing a dataset (for example, in the form of a look-up table) containing information related to unique analytes and corresponding material index values for fast processing of samples. The dataset may be updated at certain intervals of time as may be required.

It should be noted that the techniques of the present invention have been explained in terms of two distinct embodiments, namely for identification and quantification, only for the purpose of ease of understanding. In practice, various technical features explained in conjunction with these two embodiments may preferably be implemented in combination.

Figure 5:
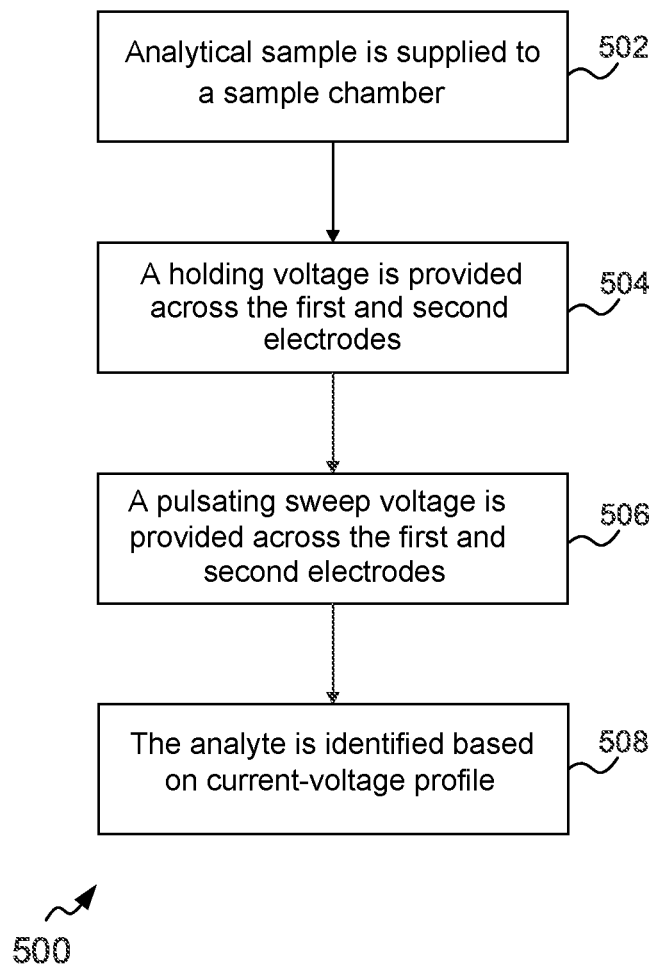
FIG. 5 illustrates a schematic view of a sensing method for identification and quantification of an analyte in an analytical sample in accordance with various exemplary embodiments of the present invention.

Referring now to FIG. 5, a schematic view of a sensing method 500 for operating the sensing device 100 for identification and quantification of an analyte in an analytical sample is depicted in accordance with various exemplary embodiments of the present invention.

In a first embodiment of the present invention, the sensing device 100 is operated in accordance with sensing method 500 to identify an analyte in an analytical sample.

At step 502, the analytical sample is supplied to a sample chamber. As explained in the preceding description, the sample chamber is at least partially delimited by a first electrode and a second electrode.

At step 504, a holding voltage is provided across the first and second electrodes such that a potential gradient is formed across the sample chamber, whereby the analyte polarizes and diffuses towards one of the electrodes forming an electrode-electrolyte interface.

At step 506, a pulsating sweep voltage is provided across the first and the second electrodes and a current-voltage profile of the analytical sample is determined.

At step 508, the analyte is identified based on the current-voltage profile.

According to the techniques of the present invention, a sample electrical mobility and a sample Debye volume is corresponding to electrical mobility and Debye volume characterizing the analytical sample are determined.

The determination of electrical mobility requires parameter values of leakage current, conductivity, and ideality parameter characterizing the analytical sample. Thus, the sample leakage current, the sample conductivity, and the sample ideality parameter are initially determined; and subsequently, the sample electrical mobility is calculated based on the sample conductivity and the sample ideality parameter.

Finally, a material index is calculated as modulus of a ratio of deviation of the sample Debye volume from a reference Debye volume and deviation of the sample electrical mobility from a reference electrical mobility. As explained earlier, the material index uniquely identifies the analyte in the analytical sample.

As explained in the preceding description, the reference Debye volume and the reference electrical mobility correspond respectively to Debye volume and electrical mobility of a reference sample, wherein the reference sample is selected from a set of reference samples based on the analytical sample.

In a second embodiment of the present invention, the sensing device 100 is operated in accordance with sensing method 500 to quantify an analyte in an analytical sample.

In this embodiment, at step 502, the analytical sample is supplied to a sample chamber. The sample chamber is at least partially delimited by a first electrode and a second electrode.

At step 504, a holding voltage is provided across the first and second electrodes such that a potential gradient is formed across the sample chamber, whereby the analyte polarizes and diffuses towards one of the electrodes forming an electrode-electrolyte interface.

As will be readily evident, the operation of sensing device 100 in this embodiment of the sensing method 500 is same as that in the preceding embodiment.

At step 506, a pulsating sweep voltage is provided across the first and the second electrodes and a capacitance-voltage profile of the analytical sample is determined.

At step 508, the analyte is quantified based on the capacitance-voltage profile.

According to the techniques of the present invention, a sample doping concentration and a sample Debye volume respectively corresponding to doping concentration and Debye volume characterizing the analytical sample are determined. As explained earlier, the sample doping concentration is calculated based on inverse of slope of capacitance ($1/C^2$) plotted against voltage (V).

In one embodiment of the present invention, the analyte quantity is determined as modulus of a ratio of deviation of the sample doping concentration from a reference doping concentration and deviation of the sample Debye volume from a reference Debye volume.

In an alternative embodiment of the present invention, if the unit volume of analyte is known, the analyte quantity is determined as modulus of a ratio of deviation of the sample Debye volume from a reference Debye volume and a unit volume of the analyte.

The details of operation of the sensing device, and in particular, various mathematical equations between the relevant electrical parameters, have already been described in detail in conjunction with FIGS. 1 through 4 and are not being explained again in conjunction with FIG. 5 for the sake of brevity.

Accordingly, the present invention provides a sensing device and a sensing method for identification and quantification of biological and chemical analytes. The techniques of the present invention facilitate label free, reliable, rapid, and low-cost identification and quantification.

The techniques of the present invention advantageously do not require elaborate sample preparation such as labelling using biomarkers, staining, and so on. Thus, the techniques of the present invention facilitate label free identification and quantification.

The sensing device and the sensing method of the present invention are advantageously not limited to any specific analytes. The techniques of the present invention are only reliant on tendency of an analyte to polarise when subjected to an electric field and hence, are applicable to identification and quantization of a wide range of analytes of interest.

The sensing device of the present invention is advantageously reusable for practically unlimited number of identification and quantification operations. Prior to each operation, the sample chamber in the sensing device may be flushed using a buffer solution such as Phosphate buffered saline to ensure no residues from a previous operation impact the measurement in the next operation.

The techniques of the present invention are conducive for in-situ applications and accordingly, facilitate characterization within a living cell rather than the conventional way of using dead cells.

While the present invention has been described in detail with reference to certain embodiments, it should be appreciated that the present invention is not limited to those embodiments. In view of the present disclosure, many modifications and variations would present themselves, to those of skill in the art without departing from the scope of various embodiments of the present invention, as described herein. The scope of the present invention is, therefore, indicated by the following claims rather than by the foregoing description. All changes, modifications, and variations coming within the meaning and range of equivalency of the claims are to be considered within their scope.

What is claimed is:

1. A sensing method for identifying an analyte in an analytical sample, said sensing method comprising:
    supplying said analytical sample to a sample chamber, said sample chamber being at least partially delimited by a first electrode and a second electrode;
    providing a holding voltage across said first and said second electrodes, such that a potential gradient is formed across said sample chamber, whereby said analyte polarizes and diffuses towards one of said electrodes forming an electrode-electrolyte interface;
    providing a pulsating sweep voltage across said first and said second electrodes and determining a current-voltage profile of said analytical sample;
    identifying said analyte based on said current-voltage profile;
    determining a sample electrical mobility and a sample Debye volume respectively corresponding to electrical mobility and Debye volume characterizing said analytical sample; and
    determining a material index as modulus of a ratio of deviation of said sample Debye volume from a reference Debye volume and deviation of said sample electrical mobility from a reference electrical mobility, wherein said material index uniquely corresponds to said analyte, whereby said analyte is identified.

2. The method according to claim 1 further comprising determining a sample leakage current, a sample conductivity, and a sample ideality parameter respectively corresponding to leakage current, conductivity, and ideality parameter characterizing said analytical sample based on said current-voltage profile; and calculating said sample electrical mobility based on said sample conductivity and said sample ideality parameter.

3. The method according to claim 1, wherein said reference Debye volume and said reference electrical mobility correspond respectively to Debye volume and electrical mobility of a reference sample, wherein said reference sample is selected from a set of reference samples based on said analytical sample.

4. A sensing method for quantifying an analyte in an analytical sample, said sensing method comprising:
supplying said analytical sample to a sample chamber, said sample chamber being at least partially delimited by a first electrode and a second electrode,
providing a holding voltage across said first and said second electrodes, such that a potential gradient is formed across said sample chamber, whereby said analyte polarizes and diffuses towards one of said electrodes forming an electrode-electrolyte interface,
providing a pulsating sweep voltage across said first and said second electrodes and determining a capacitance-voltage profile of said analytical sample,
quantifying said analyte based on said capacitance-voltage profile,
determining a sample doping concentration and a sample Debye volume respectively corresponding to doping concentration and Debye volume characterizing said analytical sample, and
determining an analyte quantity as modulus of a ratio of deviation of said sample doping concentration from a reference doping concentration and deviation of said sample Debye volume from a reference Debye volume, wherein said reference Debye volume and said reference doping concentration correspond respectively to Debye volume and doping concentration of a reference sample, wherein said reference sample is selected from a set of reference samples based on said analytical sample.

5. The method according to claim 4, wherein said sample doping concentration is calculated based on inverse of slope of capacitance ($1/C^2$) plotted against voltage (V).

6. A sensing method for quantifying an analyte in an analytical sample, said sensing method comprising:
supplying said analytical sample to a sample chamber, said sample chamber being at least partially delimited by a first electrode and a second electrode;
providing a holding voltage across said first and said second electrodes, such that a potential gradient is formed across said sample chamber, whereby said analyte polarizes and diffuses towards one of said electrodes forming an electrode-electrolyte interface;
providing a pulsating sweep voltage across said first and said second electrodes and determining a capacitance-voltage profile of said analytical sample;
quantifying said analyte based on said capacitance-voltage profile; and
determining a sample Debye volume corresponding to Debye volume characterizing said analytical sample and determining an analyte quantity as modulus of a ratio of deviation of said sample Debye volume from a reference Debye volume and a unit volume of said analyte, wherein said reference Debye volume corresponds to Debye volume of a reference sample, wherein said reference sample is selected from a set of reference samples based on said analytical sample.

7. A sensing device for identifying an analyte in an analytical sample, said sensing device comprising:
a sample chamber configured for holding said analytical sample;
a first electrode and a second electrode, said electrodes being at least partially delimiting said sample chamber;
a controlled voltage source, said controlled voltage source being electrically coupled to said first and said second electrodes, and said controlled voltage source being configured for providing a holding voltage and a pulsating sweep voltage across said first and said second electrodes, such that a potential gradient is formed across said sample chamber, and
a measurement module, said measurement module configured for measuring variation of an electrical current through said sample chamber under said pulsating sweep voltage applied across said electrodes to generate a current-voltage profile of said analytical sample, and further configured for identifying said analyte in said analytical sample based on said current-voltage profile, wherein said measurement module is configured for determining a sample electrical mobility and a sample Debye volume respectively corresponding to electrical mobility and Debye volume characterizing said analytical sample and wherein said measurement module is further configured for determining a material index as modulus of a ratio of deviation of said sample Debye volume from a reference Debye volume and deviation of said sample electrical mobility from a reference electrical mobility, wherein said material index uniquely corresponds to said analyte, whereby said analyte is identified.

8. The device according to claim 7, wherein said measurement module is further configured for determining a sample leakage current, a sample conductivity, and a sample ideality parameter respectively corresponding to leakage current, conductivity, and ideality parameter characterizing said analytical sample based on said current-voltage profile; and calculating said sample electrical mobility based on said sample conductivity and said sample ideality parameter.

9. The device according to claim 7, wherein said reference Debye volume and said reference electrical mobility correspond respectively to Debye volume and electrical mobility of a reference sample, wherein said reference sample is selected from a set of reference samples based on said analytical sample.

10. A sensing device for quantifying an analyte in an analytical sample, said sensing device comprising:
a sample chamber configured for holding said analytical sample,
a first electrode and a second electrode, said electrodes being at least partially delimiting said sample chamber,
a controlled voltage source, said controlled voltage source being electrically coupled to said first and said second electrodes, and said controlled voltage source being configured for providing a holding voltage and a pulsating sweep voltage across said first and said second electrodes, such that a potential gradient is formed across said sample chamber, and
a measurement module, said measurement module configured for measuring variation of a capacitance across said electrodes under said pulsating sweep voltage applied across said electrodes to generate a capacitance-voltage profile of said analytical sample, further configured for quantifying said analyte in said analytical sample based on said capacitance-voltage profile, and wherein said measurement module is further configured for determining an analyte quantity as modulus of a ratio of deviation of said sample doping concentration from a reference doping concentration and deviation of said sample Debye volume from a reference Debye volume, wherein said reference Debye volume and said reference doping concentration correspond respectively to Debye volume and doping concentration of a reference sample, wherein said reference sample is selected from a set of reference samples based on said analytical sample.

11. The device according to claim 10, wherein said sample doping concentration is calculated based on inverse of slope of capacitance ($1/C^2$) plotted against voltage (V).

12. A sensing device for quantifying an analyte in an analytical sample, said sensing device comprising:
- a sample chamber configured for holding said analytical sample,
- a first electrode and a second electrode, said electrodes being at least partially delimiting said sample chamber,
- a controlled voltage source, said controlled voltage source being electrically coupled to said first and said second electrodes, and said controlled voltage source being configured for providing a holding voltage and a pulsating sweep voltage across said first and said second electrodes, such that a potential gradient is formed across said sample chamber, and
- a measurement module, said measurement module configured for measuring variation of a capacitance across said electrodes under said pulsating sweep voltage applied across said electrodes to generate a capacitance-voltage profile of said analytical sample, further configured for quantifying said analyte in said analytical sample based on said capacitance-voltage profile, wherein said measurement module is further configured for determining a sample Debye volume corresponding to Debye volume characterizing said analytical sample and determining an analyte quantity as modulus of a ratio of deviation of said sample Debye volume from a reference Debye volume and a unit volume of said analyte, wherein said reference Debye volume corresponds to Debye volume of a reference sample, wherein said reference sample is selected from a set of reference samples based on said analytical sample.

* * * * *